US008571627B2

(12) United States Patent
Tremblay et al.

(10) Patent No.: US 8,571,627 B2
(45) Date of Patent: Oct. 29, 2013

(54) ECG LEAD WIRE ORGANIZER AND DISPENSER

(75) Inventors: Kathleen Tremblay, Westfield, MA (US); Linda Davis, Westfield, MA (US); Heather Knight, E. Longmeadow, MA (US); Peter Meyer, Shrewsbury, MA (US); Mark J Callahan, Medway, MA (US); Mark Tauer, Belchertown, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/471,042

(22) Filed: May 14, 2012

(65) Prior Publication Data

US 2012/0226177 A1    Sep. 6, 2012

Related U.S. Application Data

(62) Division of application No. 11/951,107, filed on Dec. 5, 2007, now Pat. No. 8,180,425.

(60) Provisional application No. 60/872,815, filed on Dec. 5, 2006.

(51) Int. Cl.
*A61B 5/0408* (2006.01)

(52) U.S. Cl.
USPC ............................ 600/382; 600/386; 600/509

(58) Field of Classification Search
USPC ........... 600/382, 386, 390, 394, 509; 439/909
See application file for complete search history.

(56) References Cited

U.S. PATENT DOCUMENTS

| 3,752,151 | A | | 8/1973 | Robichaud | |
|---|---|---|---|---|---|
| 3,805,769 | A | | 4/1974 | Sessions | |
| 3,821,496 | A | * | 6/1974 | Malone | 191/12.2 R |
| 3,828,766 | A | | 8/1974 | Krasnow | |
| 3,868,946 | A | | 3/1975 | Hurley | |
| 3,888,240 | A | | 6/1975 | Reinhold, Jr. et al. | |
| 3,901,218 | A | | 8/1975 | Buchalter | |
| 3,964,490 | A | * | 6/1976 | Nelms | 607/2 |
| 3,998,213 | A | | 12/1976 | Price | |
| 4,027,664 | A | | 6/1977 | Heavner, Jr. et al. | |
| 4,034,854 | A | | 7/1977 | Bevilacqua | |
| 4,077,397 | A | | 3/1978 | Ellis et al. | |
| 4,353,372 | A | | 10/1982 | Ayer | |

(Continued)

FOREIGN PATENT DOCUMENTS

| DE | 102004032410 | 1/2006 |
|---|---|---|
| EP | 0766946 | 4/1997 |
| EP | 1050269 | 11/2000 |

OTHER PUBLICATIONS

International Search Report EP07253850 dated Dec. 21, 2007.

(Continued)

*Primary Examiner* — Lee S Cohen
*Assistant Examiner* — Erin M Cardinal
(74) *Attorney, Agent, or Firm* — Lisa E. Winsor, Esq.

(57) ABSTRACT

An ECG lead set assembly including a lead set hub and a retractable reel assembly retained within the lead set hub. The retractable reel assembly includes a reel member adapted for rotation within the lead set hub and an electrode lead wrapped about the reel member and having an electrical conductor for connecting to an electrode for receiving biopotential signals from a patient. The electrode lead is extendable from the reel member upon rotation within the lead set hub.

10 Claims, 18 Drawing Sheets

(56) References Cited

U.S. PATENT DOCUMENTS

| | | | |
|---|---|---|---|
| 4,365,634 A | 12/1982 | Bare et al. | |
| 4,498,480 A | 2/1985 | Mortensen | |
| 4,729,377 A | 3/1988 | Granek et al. | |
| 4,763,660 A | 8/1988 | Kroll et al. | |
| 4,781,200 A | 11/1988 | Baker | |
| 4,785,822 A | 11/1988 | Wallace | |
| 4,815,964 A | 3/1989 | Cohen et al. | |
| 4,858,846 A * | 8/1989 | McDonald | 242/405.1 |
| 4,909,260 A | 3/1990 | Salem et al. | |
| 4,947,846 A | 8/1990 | Kitagawa et al. | |
| 4,957,109 A | 9/1990 | Groeger et al. | |
| 5,033,474 A * | 7/1991 | Varelis et al. | 600/509 |
| 5,224,479 A | 7/1993 | Sekine | |
| 5,263,481 A | 11/1993 | Axelgaard | |
| 5,341,806 A | 8/1994 | Gadsby et al. | |
| 5,353,793 A | 10/1994 | Bornn | |
| 5,370,116 A | 12/1994 | Rollman et al. | |
| 5,405,269 A | 4/1995 | Stupecky | |
| 5,483,967 A | 1/1996 | Ohtake | |
| 5,507,290 A | 4/1996 | Kelly et al. | |
| 5,511,553 A | 4/1996 | Segalowitz | |
| 5,546,950 A | 8/1996 | Schoeckert et al. | |
| 5,582,180 A | 12/1996 | Manset et al. | |
| 5,622,168 A | 4/1997 | Keusch et al. | |
| 5,685,303 A | 11/1997 | Rollman et al. | |
| 5,704,351 A | 1/1998 | Mortara et al. | |
| 5,724,984 A | 3/1998 | Arnold et al. | |
| 5,813,979 A * | 9/1998 | Wolfer | 600/373 |
| 5,865,740 A | 2/1999 | Kelly et al. | |
| 5,865,741 A | 2/1999 | Kelly et al. | |
| 5,913,834 A | 6/1999 | Francais | |
| 5,916,159 A | 6/1999 | Kelly et al. | |
| 5,938,597 A | 8/1999 | Stratbucker | |
| 6,006,125 A | 12/1999 | Kelly et al. | |
| 6,032,064 A | 2/2000 | Devlin et al. | |
| 6,055,448 A | 4/2000 | Anderson et al. | |
| 6,066,093 A | 5/2000 | Kelly et al. | |
| 6,070,269 A | 6/2000 | Tardif et al. | |
| 6,115,623 A | 9/2000 | McFee | |
| 6,122,536 A | 9/2000 | Sun et al. | |
| 6,122,544 A | 9/2000 | Organ | |
| 6,157,851 A | 12/2000 | Kelly et al. | |
| 6,205,355 B1 * | 3/2001 | Lomanto et al. | 600/509 |
| 6,219,568 B1 | 4/2001 | Kelly et al. | |
| 6,219,569 B1 | 4/2001 | Kelly et al. | |
| 6,232,366 B1 | 5/2001 | Wang et al. | |
| 6,240,323 B1 | 5/2001 | Calenzo, Sr. et al. | |
| 6,304,783 B1 | 10/2001 | Lyster et al. | |
| 6,327,507 B1 * | 12/2001 | Buchan | 607/115 |
| 6,339,720 B1 | 1/2002 | Anzellini et al. | |
| 6,360,119 B1 | 3/2002 | Roberts | |
| 6,400,977 B1 | 6/2002 | Kelly et al. | |
| 6,453,186 B1 | 9/2002 | Lovejoy et al. | |
| 6,456,872 B1 | 9/2002 | Faisandier | |
| 6,553,246 B1 | 4/2003 | Wenger | |
| 6,553,250 B2 | 4/2003 | Rantala | |
| 6,564,079 B1 | 5/2003 | Cory et al. | |
| 6,611,705 B2 | 8/2003 | Hopman et al. | |
| 6,623,312 B2 | 9/2003 | Merry et al. | |
| 6,636,754 B1 | 10/2003 | Baura et al. | |
| 6,647,286 B1 | 11/2003 | Kato et al. | |
| 6,654,626 B2 | 11/2003 | Devlin et al. | |
| 6,748,797 B2 | 6/2004 | Breed et al. | |
| 6,751,493 B2 | 6/2004 | Wenger | |
| 6,768,921 B2 | 7/2004 | Organ et al. | |
| 6,816,744 B2 | 11/2004 | Garfield et al. | |
| 6,847,836 B1 | 1/2005 | Sujdak | |
| 6,970,731 B1 | 11/2005 | Jayaraman et al. | |
| 6,973,341 B2 | 12/2005 | Watson | |
| 6,973,343 B2 | 12/2005 | Wenger | |
| 6,980,852 B2 | 12/2005 | Jersey-Willuhn et al. | |
| 7,037,114 B1 | 5/2006 | Eiger et al. | |
| 7,039,460 B2 * | 5/2006 | Ryczek | 607/5 |
| 7,104,801 B1 | 9/2006 | Brodnick et al. | |
| 7,150,655 B2 | 12/2006 | Mastrototaro et al. | |
| 7,169,107 B2 | 1/2007 | Jersey-Willuhn et al. | |
| 7,184,820 B2 | 2/2007 | Jersey-Willuhn et al. | |
| 7,197,357 B2 | 3/2007 | Istvan et al. | |
| 7,206,630 B1 | 4/2007 | Tarler | |
| 7,272,428 B2 | 9/2007 | Hopman et al. | |
| 7,319,895 B2 | 1/2008 | Klefstad-Sillonville et al. | |
| 7,333,850 B2 | 2/2008 | Marossero et al. | |
| 2002/0072682 A1 | 6/2002 | Hopman et al. | |
| 2002/0133069 A1 | 9/2002 | Roberts | |
| 2002/0188216 A1 | 12/2002 | Kayyali et al. | |
| 2004/0073127 A1 | 4/2004 | Istvan et al. | |
| 2004/0127802 A1 | 7/2004 | Istvan et al. | |
| 2004/0176674 A1 | 9/2004 | Nazeri | |
| 2005/0085736 A1 | 4/2005 | Ambrose et al. | |
| 2005/0177052 A1 | 8/2005 | Istvan et al. | |
| 2005/0203349 A1 | 9/2005 | Nanikashvili | |
| 2006/0073728 A1 | 4/2006 | Zaiken et al. | |
| 2006/0117805 A1 | 6/2006 | Valentine et al. | |
| 2007/0027388 A1 | 2/2007 | Chou | |
| 2007/0038057 A1 | 2/2007 | Nam et al. | |
| 2007/0260133 A1 | 11/2007 | Meyer | |
| 2007/0282350 A1 | 12/2007 | Hernest | |
| 2008/0058876 A1 * | 3/2008 | Barolat | 607/3 |
| 2008/0143080 A1 | 6/2008 | Burr | |

OTHER PUBLICATIONS

International Search Report EP07251765 dated Mar. 31, 2008.
International Search Report EP07254691 dated Mar. 25, 2008.
International Search Report EP08164409 dated Jan. 27, 2009.
Andreas Boos et al.; "A New Lightweight Fetal Telemetry System"; Dec. 1995; Hewlett-Packard Journal; pp. 82-93.

* cited by examiner

ECG LEAD WIRE ORGANIZER AND DISPENSER

CROSS-REFERENCE TO RELATED APPLICATION(S)

This application is a divisional of and claims the benefit of priority under 35 U.S.C. §120 to U.S. patent application Ser. No. 11/951,107 filed Dec. 5, 2007 entitled ECG LEAD WIRE ORGANIZER AND DISPENSER, now U.S. Pat. No. 8,180,427 issued May 15, 2012, which claims priority to and the benefit of U.S. Provisional Patent Application No. 60/872,815 filed in the U.S. Patent and Trademark Office on Dec. 5, 2006, each of which is incorporated by reference in its entirety for all purposes.

BACKGROUND

1. Technical Field

The present disclosure relates to medical equipment. In particular, the present disclosure relates to an ECG lead wire organizer and dispenser, and methods for use thereof.

2. Description of Related Art

Electrocardiograph (ECG) monitors and recorders (hereinafter "ECG Monitors") are widely used to obtain biopotential signals containing information indicative of the electrical activity associated with the heart and pulmonary system. To obtain biopotential signals, ECG electrodes are applied to the skin of a patient in various locations and coupled to an ECG monitor. Placement of the electrodes is dependant on the information sought by the clinician.

The placement of the ECG electrodes on the patient has been established by medical protocols. The most common protocols require the placement of the electrodes in a 3-lead, a 5-lead or a 12-lead configuration. A 3-lead configuration requires the placement of three electrodes; one electrode adjacent each clavicle bone on the upper chest and a third electrode adjacent the patient's lower left abdomen. A 5-lead configuration requires the placement of the three electrodes in the 3-lead configuration with the addition of a fourth electrode adjacent the sternum and a fifth electrode on the patient's lower right abdomen. A 12-lead configuration requires the placement of 10 electrodes on the patient's body. Four electrodes, which represent the patient's limbs, include the left arm electrode (LA), the right arm electrode (RA), the left leg electrode (LL), and the right leg electrode (RL). Six chest electrodes (V1-V6 leads) are placed on the patient's chest at various locations near the heart. Three additional references are constructed from measurements between the right arm and left arm (Lead I), the right arm and the left leg (Lead II) and the left arm to left leg (Lead III). The ten electrodes provide 12 measurement points consisting of I, II, III, AVR, AVL, AVF, and V1-V6 with the right leg electrode typically used as a ground.

The electrodes, after being positioned on the patient, connect to an ECG monitor by an ECG lead set. The distal end of the ECG lead set, or portion closest to the patient, connects to each electrode (alternatively, the electrodes may be integrated into the distal end of the ECG lead set) and receives biopotential signals from the body. The proximal end of the ECG lead set connects to the ECG input connector and supplies the biopotential signals received from the body to the ECG monitor.

Proper placement of the ECG electrodes and proper connections of the ECG electrodes to the ECG lead sets is critical for obtaining the correct biopotential signals. Clinicians often have difficulty connecting ECG lead sets to ECG electrodes because the individual wires of the ECG lead set often become entangled or because the clinician must determine which individual wire connects to each electrode. In addition, the individual wires of the ECG lead sets are often long and cumbersome resulting in patient discomfort.

Issues with placement of electrodes and connection of the ECG lead set are often compounded during emergency situations. First responders and clinicians often place ECG electrodes on accident victim or heart attack sufferers to establish the medical condition. Any delay may result in adverse consequences. Other emergency treatments may require the rapid removal of ECG electrodes further compounding the issues with entanglement and re-connection.

During use, individual electrodes or one or more of the individual wires of the ECG lead sets may become damaged. Individual electrodes may be replaced provided the ECG lead set connects to the electrodes via an electrode connector. Individual wires of the ECG lead set sometimes cannot be replaced and damage thereof may require the replacement of the entire ECG lead set.

The present application provides an ECG lead set organizer, dispenser and methods of use thereof that preventing the aforementioned problems.

SUMMARY

The present disclosure relates to medical equipment. In particular, the present disclosure relates to an ECG lead set organizer, dispenser and methods of use thereof. In accordance with one preferred embodiment, an ECG lead set apparatus includes a lead set hub adapted for electrical connection to a biomedical device and being adapted for positioning relative to a patient and at least one lead wire having hub end for releasable connection to the lead set hub and an electrode at another end for receiving biopotential signals from the patient. The biopotential signals are transmittable through the lead set hub to provide biomedical information to the biomedical device. A plurality of lead wires may be provided with each lead wire having an electrode. At least one lead wire defines an effective length between the hub connector and the electrode with the effective length being adjustable. A slide adjuster may be mounted about the lead wire. The slide adjuster is adapted to slide along the lead wire to adjust the effective length. The slide adjuster may be a buckle member.

At least one lead wire may be extensible. The at least one lead wire may include a general serpentine arrangement adapted to flex toward a linear arrangement to thereby adjust the effective length thereof. The at least one lead wire may be encased within an insulative cover. The at least one wire may be adapted to flex toward the linear arrangement within the insulative cover. The insulative cover may be adapted to stretch.

In another embodiment, the lead set hub may include an electrode mounted thereto. A plurality of electrodes may be mounted to the lead set hub. An electrode array may be connectable to the lead set hub. The electrode array may include a substrate and a plurality of electrodes mounted to the substrate.

As a further alternative, a clamp may be mounted to the lead set hub. The clamp has a receptacle for reception of the hub end of the at least one lead wire. The clamp is movable from an initial position to a clamping position to secure the hub end to the lead set hub and establish electrical connection between the electrodes and the biomedical device. The clamp includes a conductive terminal adapted to electrically contact the at least one lead wire upon movement of the clamp to the clamping position. The at least one lead wire may include an insulating cover. The clamp may include a penetrating member adapted to penetrate the insulating cover upon movement of the clamp to the clamping position to permit the conductive terminal to electrically contact the at least one lead wire. The penetrating member may be adapted to sever the at least one lead wire upon movement of the clamp to the clamping position.

In another embodiment, an ECG lead set apparatus includes a lead set hub adapted for electrical connection to a biomedical device and being adapted for positioning relative to a patient, at least one lead wire having hub end for connection to the lead set hub and an electrode at another end for receiving biopotential signals from the patient. The biopotential signals are transmittable through the lead set hub to provide biomedical information to the biomedical device. A reel is disposed within the lead set hub and houses the at least one lead wire. The at least one lead wire is releasable from the reel to vary the effective length between the electrode and the lead set hub.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail. As used herein and as is traditional, the term "distal" refers to the portion which is furthest from the user/clinician and the term "proximal" refers to the portion that is closest to the user/clinician. In addition, terms such as "above", "below", "forward", "rearward", etc. refer to the orientation of the figures or the direction of components and are simply used for convenience of description.

Figure 1:
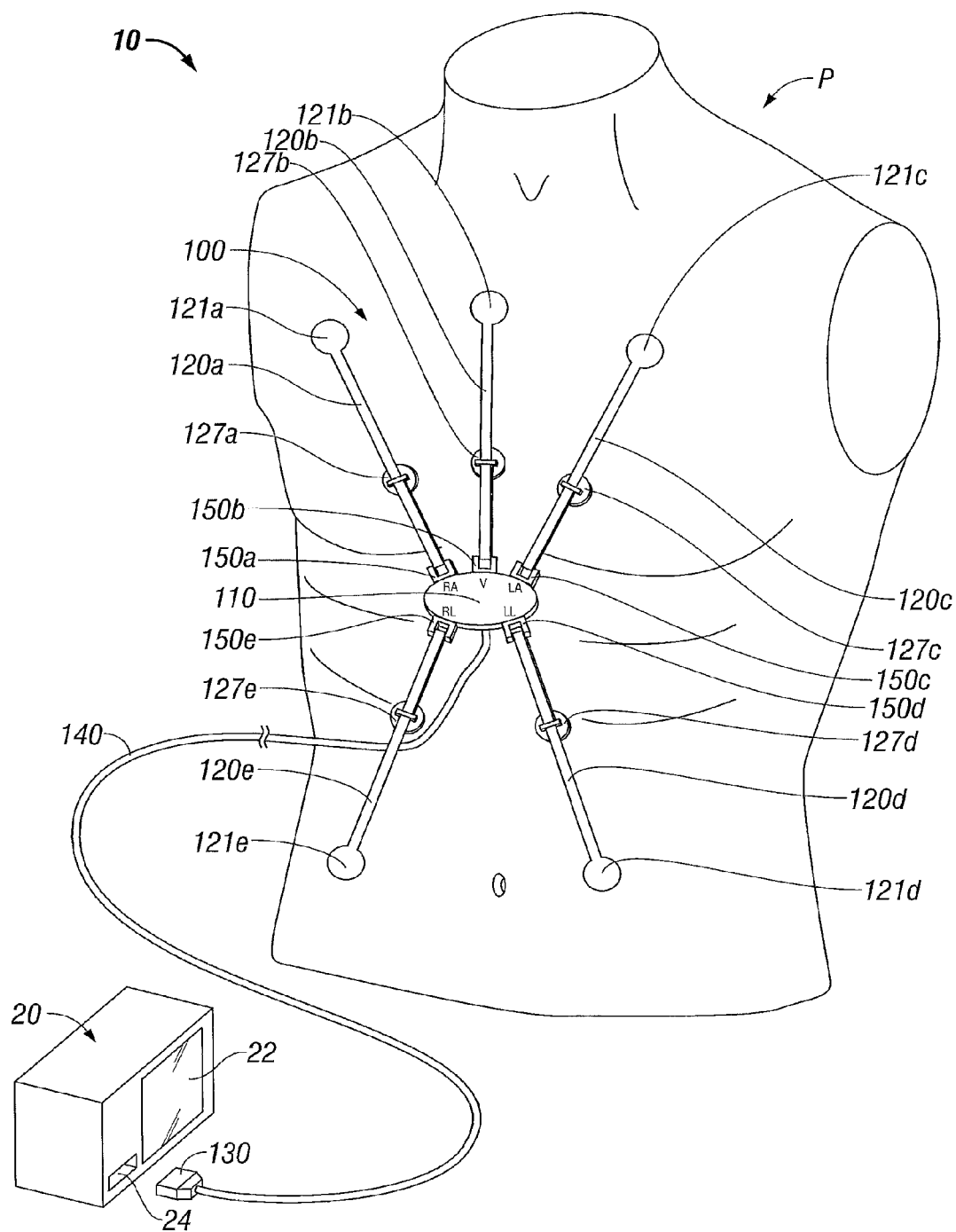
FIG. 1 is a schematic illustrating an ECG monitoring system incorporating an ECG monitor and an ECG lead set assembly in accordance with the present disclosure and disposed on a patient.

FIG. 1 illustrates, in schematic view, an ECG monitoring system 10 in accordance with the principles of the present disclosure. ECG monitoring system 10 includes ECG monitor 20 and ECG lead set assembly 100 in electrical communication with the ECG monitor 20. ECG monitor 20 is configured to receive biopotential signals containing information indicative of the electrical activity associated with the heart and pulmonary system and to display the information on user display 22. ECG monitor 20 include at least one lead set input connector 24 configured to connect to at least one ECG lead set assembly 100 through cable 140. Connector 130 on the proximal end of cable 140 electrically and/or mechanically connects lead set assembly 100 to ECG monitor 20. Alternatively, connector 130 may connect to ECG monitor 20 through an adapter (not shown).

Figure 1A:
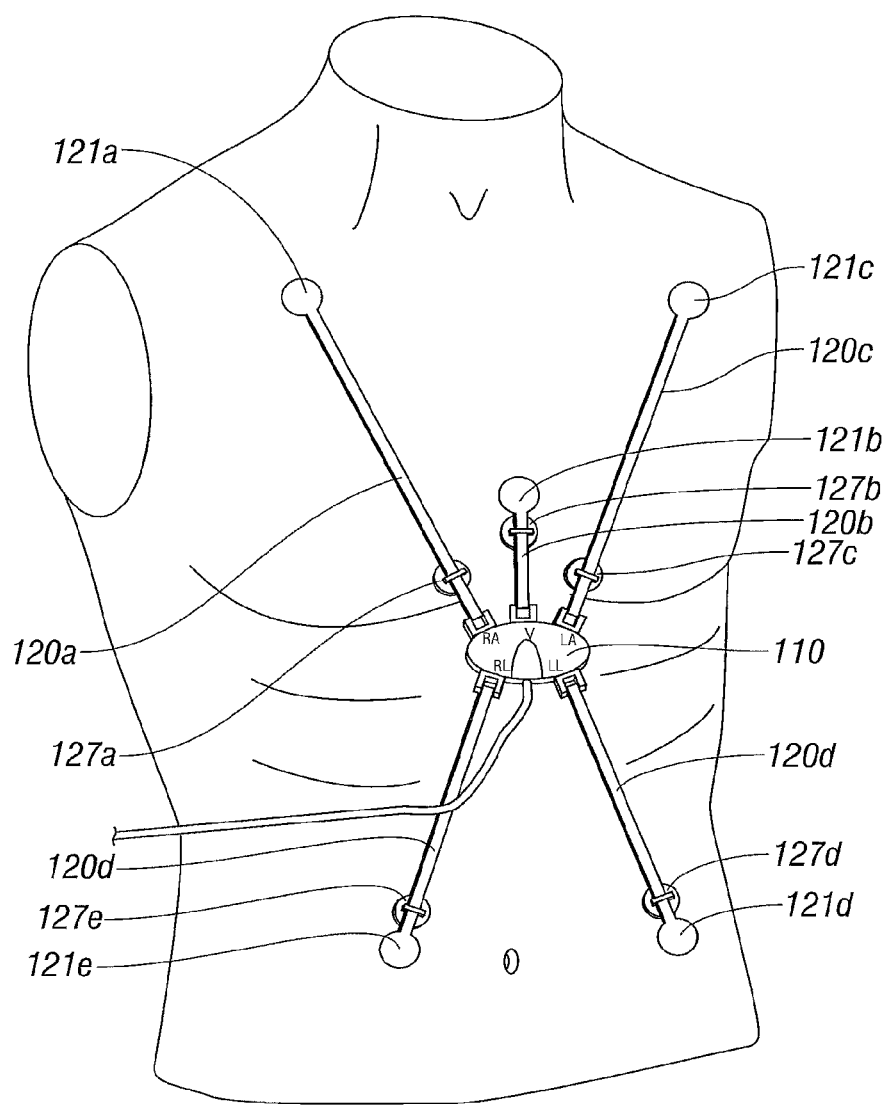
FIG. 1A is another schematic illustrating an alternate arrangement of an ECG lead set assembly of the ECG monitoring system of FIG. 1.

ECG lead set assembly 100 includes lead set hub 110 and one or more ECG electrode leads 120a-e releasably connected to the lead set hub 110. ECG electrode leads 120a-e has electrodes 121a-e respectively connected thereto. Electrodes 121a-e may be individual components releasably connectable to electrode leads 120a-e via suitable electrode connectors. Alternatively, the electrodes 121a-e may be integrally formed as an integral component of the respective electrode leads 120a-e. In the illustrated embodiment, ECG lead set assembly 100 is configured in a 5 lead configuration. However, ECG lead set 100 may be configured in any suitable configurations. Cable 140 is connected to lead set hub 110 through a suitable electrical connector or adapter. FIG. 1A illustrates one arrangement of the ECG lead set 100 suitable in a 5 lead ECG configuration.

Figure 2A:
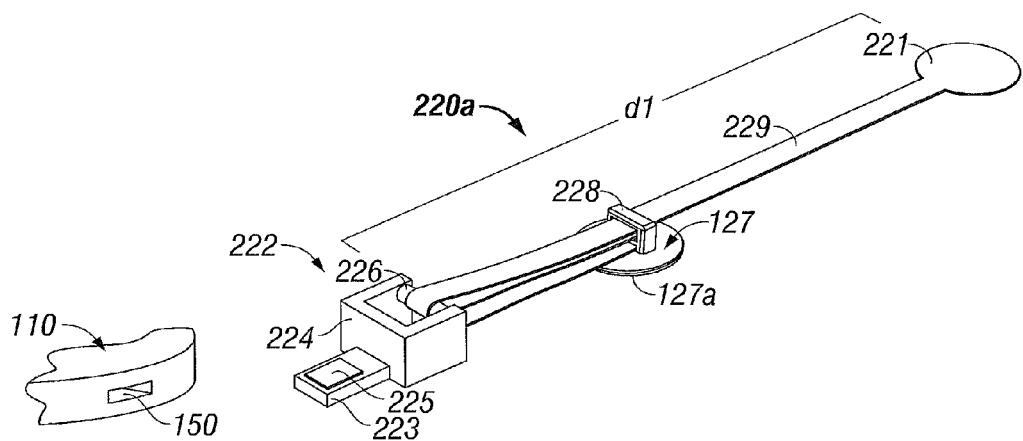
FIG. 2A is a perspective view of one embodiment of an ECG electrode lead of the ECG lead set assembly of FIG. 1.
Figure 2B:
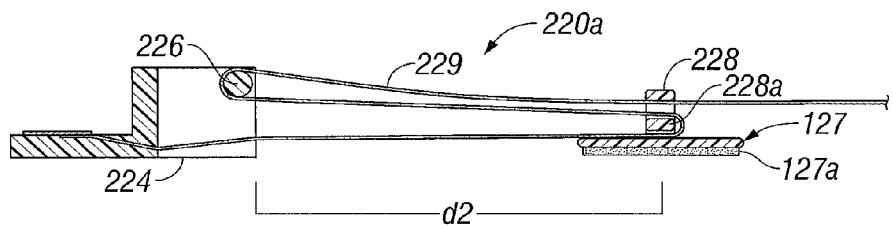
FIG. 2B is a cross-sectional view of the ECG electrode lead of FIG. 2A.

Referring now to FIGS. 1 and 2A-2B, in one embodiment, lead set hub 110 includes at least one, preferably a plurality of, receptacles 150a-e configured to releasably connect to respective ECG electrode leads 120a-e. The proximal end of each of ECG electrode leads 120a-e detachably connects to a corresponding receptacle 150*a-e* on lead set hub 110. An exemplative ECG electrode lead 220*a* depicted in FIGS. 2A-2B includes plug assembly 222, slide adjuster 127*a*, conductive signal conducting web 229 and electrode 221. Plug 222 includes electrical contact 225 disposed on tab 223 and plug barrel 226 disposed in barrel housing 224. Tab 223 detachably connects to receptacle 150 on lead set hub 110. Electrical contact 225 forms an electrical connection between lead set hub 110 and ECG electrode lead 220*a*. Tab 223 in FIG. 2A forms an interference fit connection with receptacle 150 and secures tab 223 in receptacle. The interference fit is adapted to provide a sufficient electrical connection between electrical contact 225 and lead set hub 110. Other suitable means of connection may be used, such as, for example, a locking-tab connection, a barrel/pin connection, or a snap connection.

Web 229 connects to barrel housing 224 of plug assembly 222 and electrically connects to electrical contact 225 through barrel housing and tab 223, thus forming an electrical connection between electrode 221 and the electrical contact 225. Web 229 is capable of forming a bending radius equal to the radius of the adjustment slide barrel 228*a*. Web 229 may be a single or multi-conductor ribbon cable, with at least one electrical trace printed on a flexible substrate or any other suitable wire or ribbon-type cable.

Slide adjuster 127 includes adhesive pad 127*a* for securing slide adjuster 127 to patient skin, web guide 228 and adjustment slide barrel 228*a* housed in the web guide 228. Web guide 228 positions and/or guides web 229 through slide adjuster 127. Slide adjuster 127 is slidably disposed on web 229. Web 229 is received within web guide 228 and at least partially wraps around adjustment slide barrel 228*a*.

The distance "d1" between electrode 221 and plug 222 may be adjusted by positioning slide adjuster 127 relative to the plug 222. Decreasing the distance "d2" between slide adjuster 127 and plug 222 increases the distance "d1" between the electrode 221 and the plug 222. Increasing the distance "d2" between slide adjuster 127 and plug 222 decreases the distance "d1" between the electrode 221 and the plug 222.

ECG electrode lead 220*a* in FIGS. 2A and 2B is configured such that web 229 at least partially wraps around each of adjustment slide barrel 228*a* and plug barrel 226. The distance "d1" between electrode 221 and plug 222 may be adjusted between a length about equal to the length of web 229 to a distance about equal to a third of the length of the web 229.

In use, again with reference to FIGS. 1 and 2A, lead set hub 110 is disposed on the chest of the patient "p". Lead set hub 110 may be disposed on patient "p" or may be adhered to patient "p" with a suitable material, such as, for example, adhesive or conductive hydrogel. Alternatively, the bottom or patient side of lead set hub 110 may include a medical electrode (not shown), and that secures the lead set hub 110 to patient "p".

Tab 223 of plug 222 on each ECG electrode leads 120*a-e* connects to a receptacle 150*a-e* of lead set hub 110 and electrodes 121*a-e* are disposed on the patient "p". Slide adjuster 227 of each ECG electrode lead 120*a-e* is positioned such that the length of the ECG electrode lead 120*a-e* is customized to fit the patient "p" and adhesive pad 227*a* on slide adjuster is adhered to patient "p".

The clinician may replace or remove any of the individual ECG electrode leads 120*a-e* of the ECG lead set assembly 100 without replacing the entire lead set. For example, if any ECG lead 120*a-e* is found to be malfunctioning, the clinician may remove the ECG lead 120*a-e* and replace it with another lead 120*a-e*. The clinician may also disconnect the individual ECG electrode lead 120*a-e* from receptacles 150*a-e* of lead set hub 110 during medical procedures that require isolation of ECG electrodes 121*a-e*.

While plug 222 is configured to be removable from receptacle 150*a-e*, and is therefore reusable, it is desirable to limit the reusability of ECG electrode lead 120*a-e* and/or lead set hub 110 to a single patient to prevent cross-contamination or re-use. Plug 222 and/or receptacle 150*a-e* may be configured to limit the number of times they may be reused. Mechanical wear between receptacle 150*a-e* and electrical contact 225 or receptacle 150*a-e* and/or plug 222 may limit the number of uses, or receptacle 150*a-e* and/or plug 222 may be configured to fail after a single use.

Various other suitable configurations may be used to provide adjustability of the lengths of ECG electrode lead 120*a-e*. ECG electrode lead 220*c* illustrated in FIG. 2C includes first and second slide adjusters 227*b*, 227*c*. Web 229 connects to plug assembly 222*c* on the proximal end, passes through first slide adjuster 227*b*, at least partially wraps around second adjustment slide barrel 228*c*, at least partially wraps first adjustment slide barrel 228*b* and passes through the second slide adjuster 227*c*. On the distal end, web 229 connects to electrode 221 or to a suitable electrode connector (not shown).

Figure 2C:
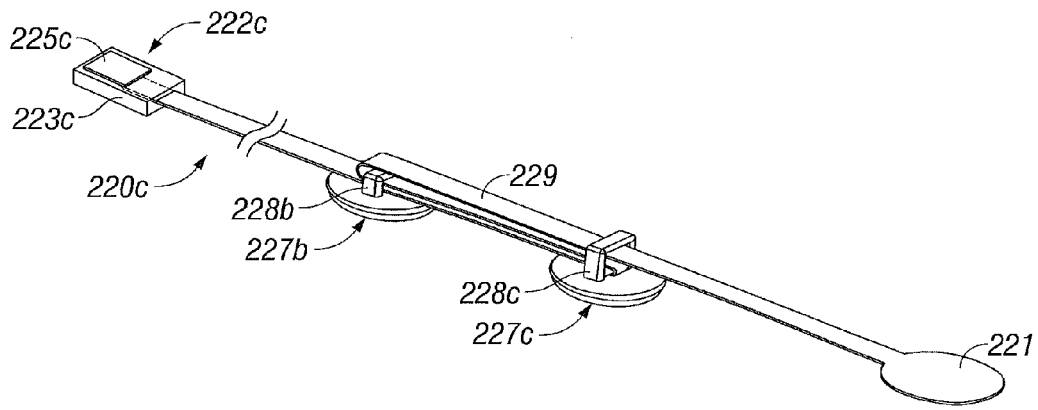
FIG. 2C is a perspective view of another embodiment of an ECG electrode lead for use with the ECG lead set assembly.

Plug assembly 222*c* of FIG. 2C consists of tab 223*c* and electrical contact 225*c* and is smaller in size than plug assembly 222 of ECG electrode lead 220*a* of FIGS. 2A and 2B, and thus tab 223*c* presents a smaller profile when positioned on the patient. The distance between electrode 221 and plug 222*c* may be adjusted to a length about equal to the length of the web 229 to a distance about equal to a third of the length of the web 229.

Figure 3A:
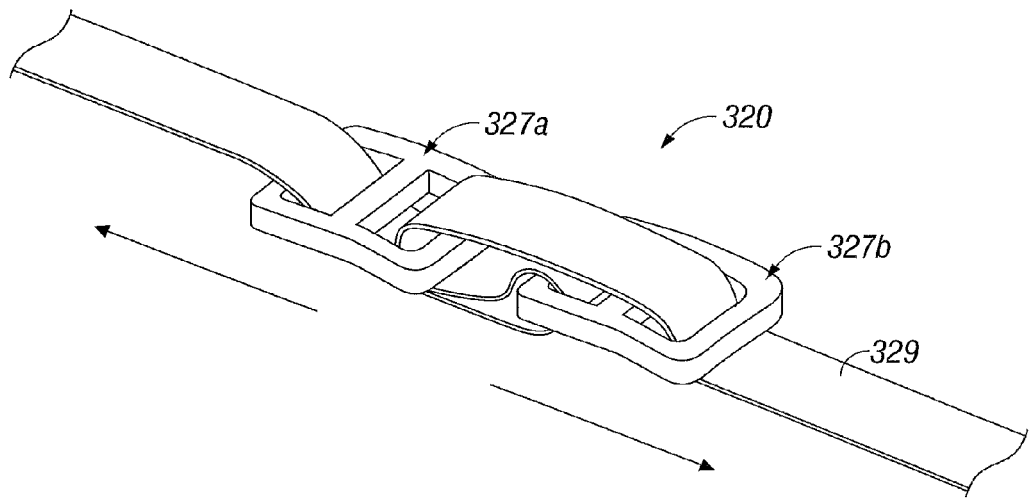
FIG. 3A is a perspective view of another embodiment of an ECG electrode lead useable with the ECG lead set assembly of FIG. 1.
Figure 3B:
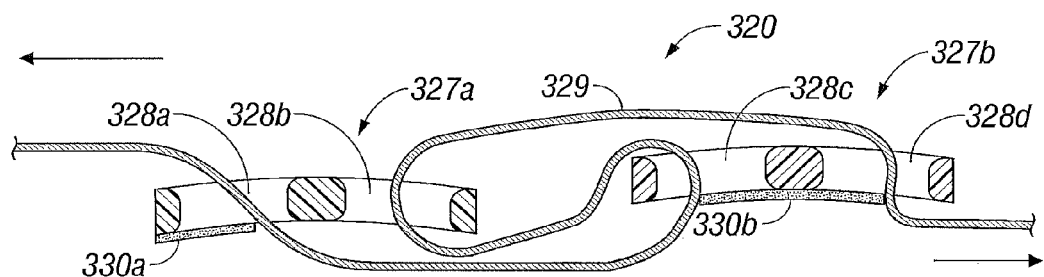
FIG. 3B is a cross-sectional view of the ECG electrode lead of FIG. 3A.

FIGS. 3A-3B illustrate yet another embodiment of an ECG electrode lead of the present disclosure. ECG electrode lead 320 includes one or more buckle-type slide adjusters 327*a*, 327*b* configured to guide and/or position the web. Buckle-type slide adjuster 327*a*, 327*b* form one or more slots 328*a-d*. Web 329 passes through a first slot 328*a* of first buckle-type slide adjuster 327*a*, through first slot 328*c* of second buckle-type slide adjuster 327*b*, through second slot of the first buckle-type slide adjuster 327*a* and through second slot of the second buckle-type slide adjuster 327*b*.

Buckle-type slide adjusters 327*a*, 327*b* are configured to provide a means of adjusting the length of the ECG electrode lead 320. The length of the ECG electrode lead 320 may be adjusted to a length about equal to the length of web 329 to a length about equal to a third of the length of the web 329.

At least a portion of buckle type slide adjuster 327*a*, 327*b* adjacent to patient's skin may include a coating and/or layer of a suitable adhesive or gel material configured to adhere to the patient's skin. The proximal portion adhesive layer 330*a* of first buckle-type slide adjuster 327*a* and middle portion adhesive layer 330*b* of second buckle-type slide adjuster 327*b* attach each of buckle-type slide adjusters 327*a*, 327*b* to patient skin and may prevent further adjustments to the length of the ECG electrode lead 320. Buckle-type slide adjuster 327*a*, 327*b* may include a snap-down locking device (not shown) to further prevent the further adjustments to the length of the ECG electrode lead 320.

Alternatively, ECG electrode assembly may include a single buckle with a second adjuster incorporated into the plug, similar to plug 222 illustrated in FIGS. 2A and 2B. A single buckle may allow one-handed adjustment to the length of the ECG electrode assembly.

Figure 3C:
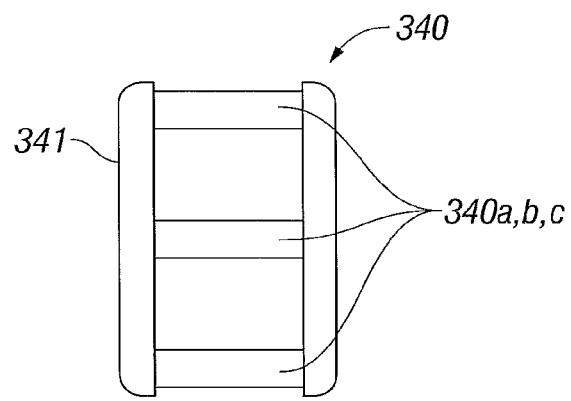
FIG. 3C is a plan view of a tri-slide adjuster for use with the ECG electrode lead.
Figure 3D:
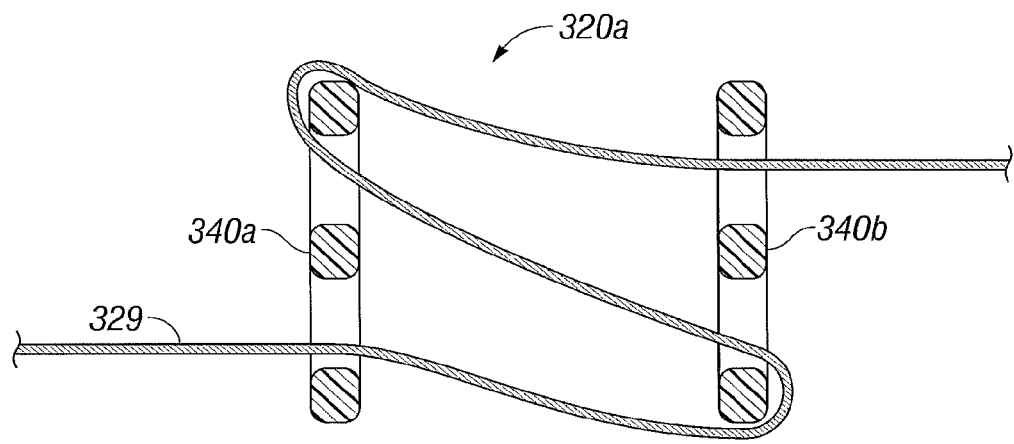
FIGS. 3D-3E are cross-sectional views illustrating the use of the tri-slide adjuster of FIG. 3C adjusting the length of the signal conducting web.
Figure 3E:
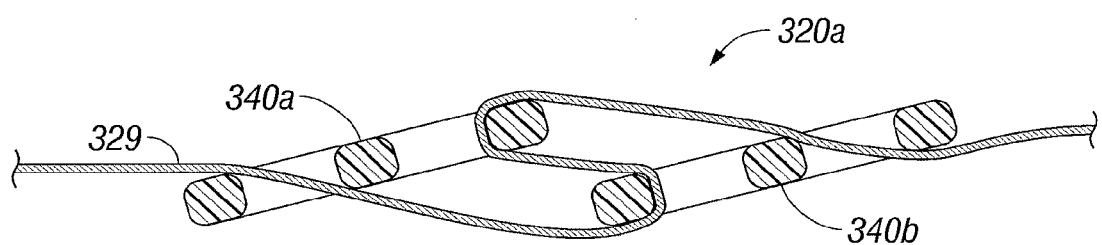

FIGS. 3C-3E illustrate yet another embodiment of slide adjusters that may be used with an ECG electrode lead set assembly of the present disclosure. FIG. 3C is a plan view of tri-slide adjuster 340 that includes a tri-slide housing and first, second and third tri-slide barrels 340a-c. FIGS. 3D and 3E illustrate an ECG electrode assembly 320 including two tri-slide adjusters 340.

In FIG. 3D, first and second tri-slide adjusters 340a, 340b are positioned perpendicular to web 329 and web 329 slides freely through and around the tri-slide barrels 326a-c of the tri-slide adjusters 340a, 340b. The length of the ECG electrode lead 320 may be adjusted by varying the distance between the first and second tri-slide adjusters 340a, 340b.

In FIG. 3E, first and second tri-slide adjusters 340a, 340b are not positioned perpendicular to web 329. Tri-slide adjusters 340a, 340b not positioned perpendicular to web 329 restrict the web 329 and prohibit adjustment to the length of the ECG electrode assembly 320.

Figure 4A:
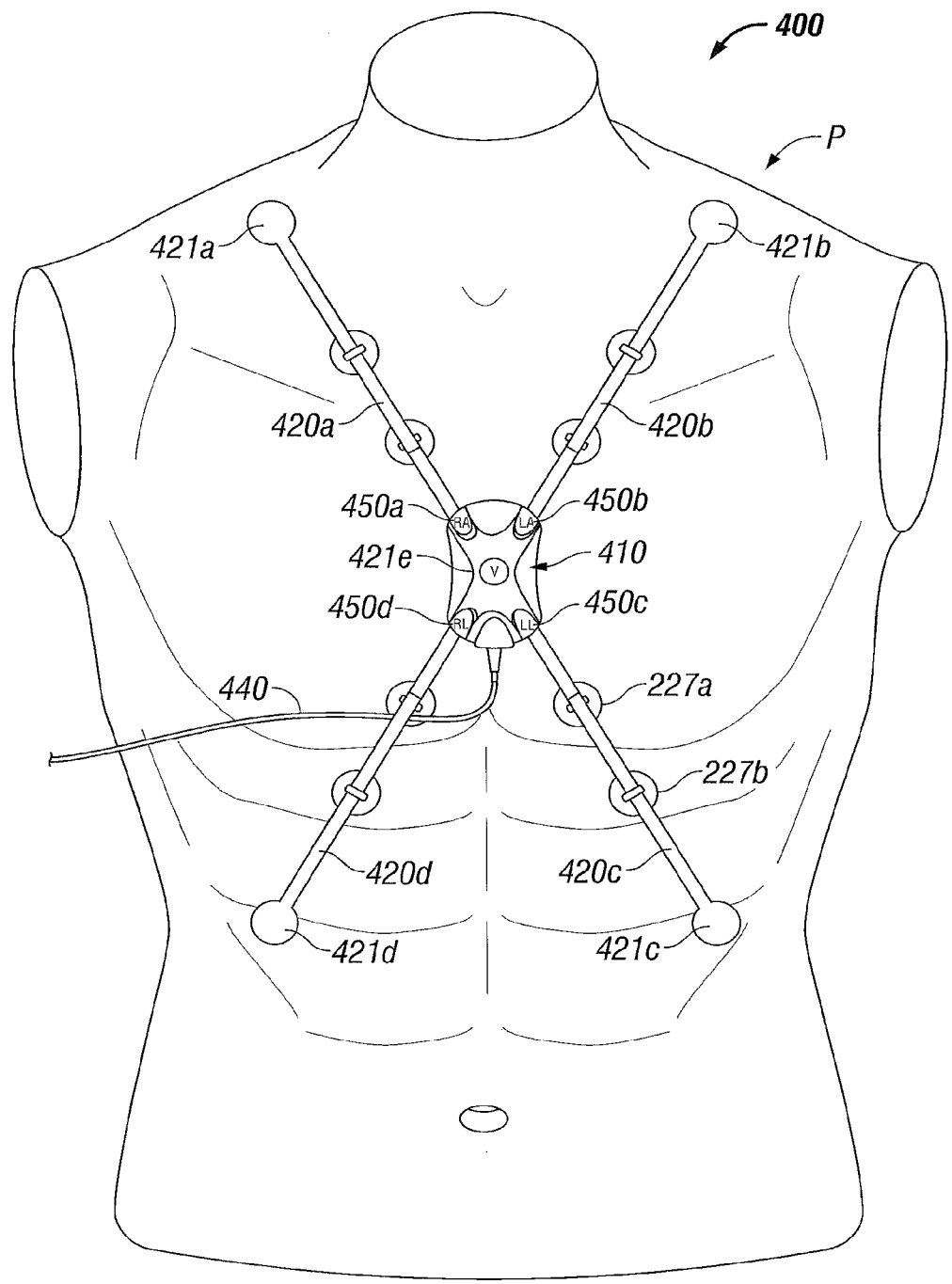
FIG. 4A is a schematic illustrating an alternate embodiment of an ECG lead set assembly including the ECG electrode lead of FIG. 2C disposed on a patient.

Referring now to FIG. 4A, another embodiment of ECG lead set 400 according to the present disclosure is illustrated. FIG. 4A illustrates ECG lead set 400 with four ECG electrode leads 420a-d of FIG. 2C connected to lead set hub 410. Receptacles 450a-d on lead set hub 410a are configured to receive the plug assembly (not shown) of ECG electrode leads 420a-d. Electrodes 421a-e are disposed on patient "p" and first and second slide adjusters 227a, 227b are positioned to take up access web 229. The 5 electrodes 421a-e of the ECG lead set 400 are configured in a 5 lead configuration. ECG lead set 400 may be configured in other suitable configurations.

Figure 4B:
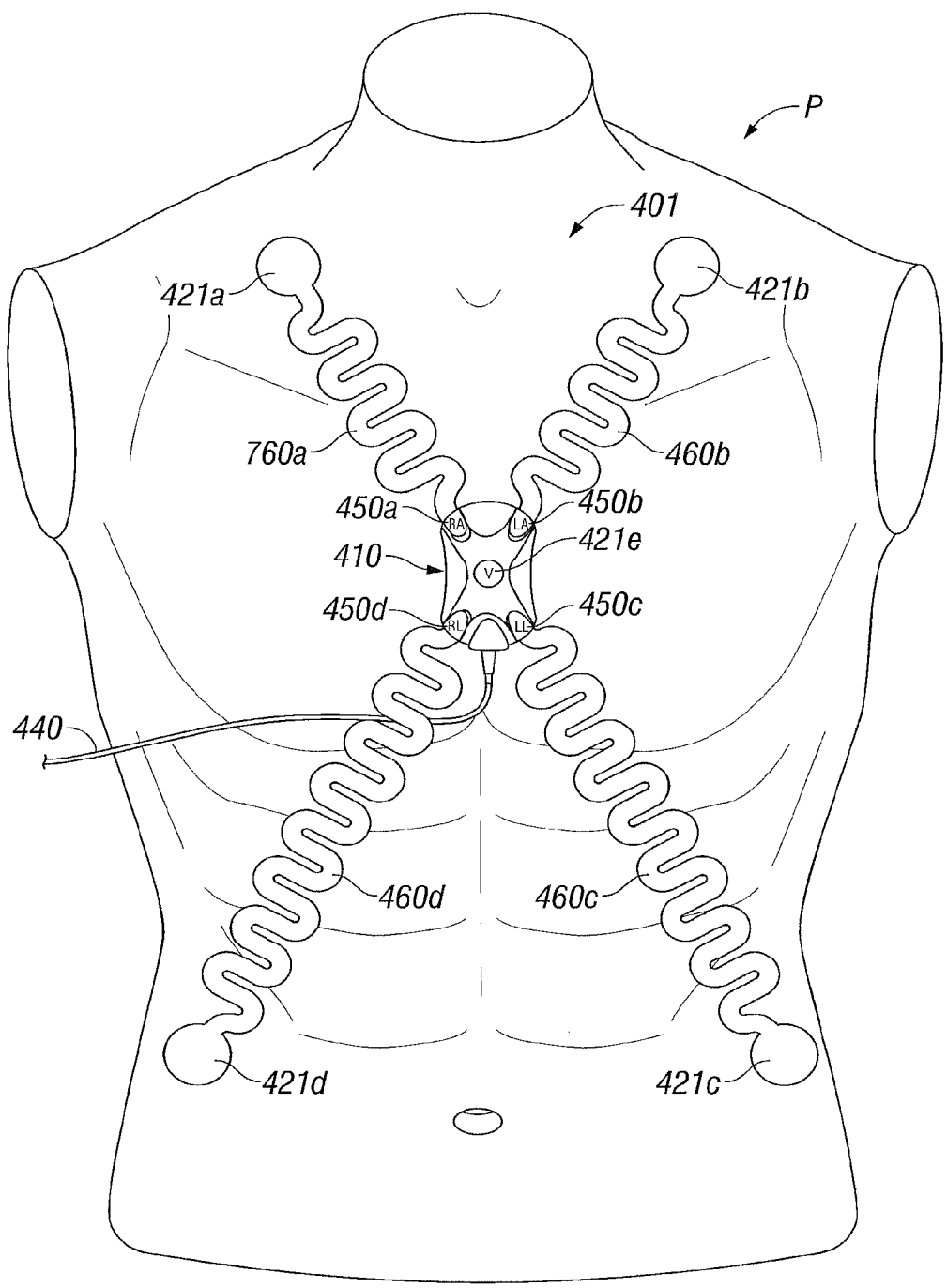
FIG. 4B is a schematic illustration of another embodiment of an ECG lead set assembly including extendable ECG electrode leads disposed on a patient.

FIG. 4B illustrates ECG lead set 401 with four extendable ECG electrode leads 460a-d connected to lead set hub 410 and cable 440. The 5 electrodes 421a-e of the ECG lead set 401 are configured in a 5 lead configuration. ECG lead set 401 may be configured in other suitable configurations.

Extendable ECG electrode assemblies 460a-d may be formed from a flexible substrate die cut into a serpentine pattern with an electrical trace printed onto the substrate. Substrate may be extended to provide sufficient length for placement of electrodes 421a-d away from lead set hub 410b. Alternatively, extendable ECG electrode leads 460a-d may be formed from a suitable serpentine-shaped cable. Extendable ECG electrode leads 460a-d may include additional layers to provide EMI shielding. Extendable ECG electrode leads 460a-d may be formed to any suitable length.

Figure 4C:
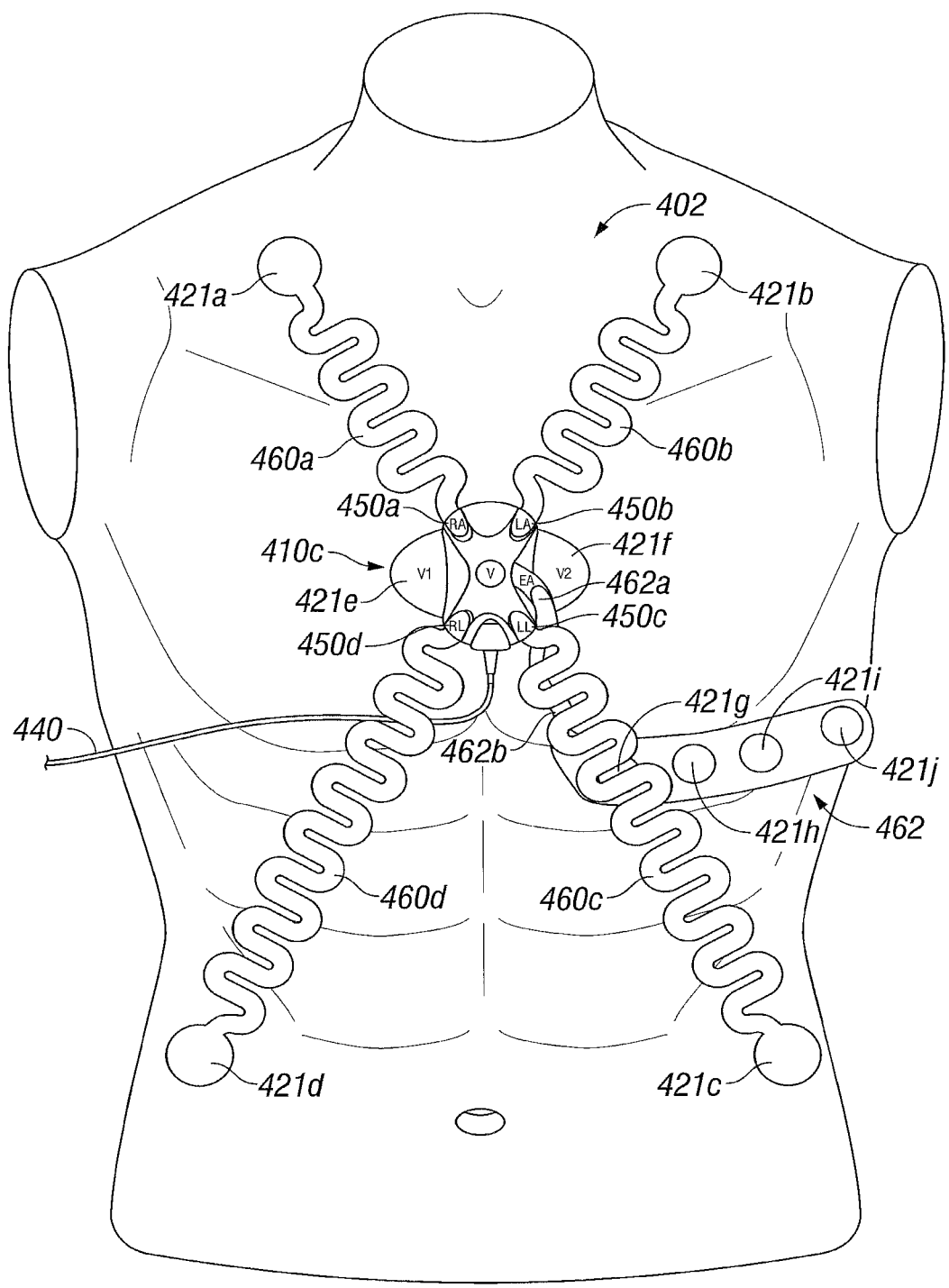
FIG. 4C is a schematic illustration of another embodiment of an ECG lead set including the extendable ECG electrode assemblies of FIG. 4B, an electrode lead set hub and an electrode array.

FIG. 4C illustrates an ECG lead set 402 with the extendable ECG electrode leads 460a-d from FIG. 4B, electrode lead set hub 410c, cable 440 and electrode array 462 configured to connect to the electrode lead set hub 410c. The 10 electrodes 421a-j of the ECG lead set 402 are configured in a 12-lead configuration. ECG lead set 402 may be configured in other suitable configurations.

Electrode lead set hub 410c includes one or more electrode tabs 421e, 421f, configured to attach to patient "p" and receive electrical signals. Electrode tabs 421e, 421f may be integrated into a disposable electrode lead set hub 410c. Alternatively, electrode lead set hub 410c may be reusable and electrode tabs 421e, 421f may be electrically and/or mechanically attached to electrode lead set hub 410c. Means of attachment may be adhesive, hook-and-loop fasteners, slotted tabs, an electrical plug and receptacle or any other suitable means of electrically and mechanically attaching an electrode.

Electrode array 462 includes one or more electrode 421g-j disposed on a flexible substrate and configured to receive electrical signals from patient "p". Electrode array 462 may include extendable portion 462b configured to extend to electrode lead set hub 410c. Electrode array receptacle 462a is configured to receive plug (not shown) on the proximal end of extendable portion 462b of electrode array 462. Electrode array receptacle 462a may receive a plurality of electrical signals from electrodes 421g-j on electrode array 462.

Application of the ECG lead set 402 is effected by first disposing electrode lead set hub 410c on the center chest portion of patient "p". Backing (not shown), if present, of each electrode tab 421e, 421f is removed and electrode tabs 421e, 421f are applied to patient "p" skin. After electrode lead set hub 410c is disposed, clinician applies one or more electrode 421g-j of electrode array 462 to patient. If necessary, extendable portion 462b of electrode array 462 is extended to enable connecting the plug (not shown) on the proximal end of electrode array 462 to connect to electrode array receptacle 462b. Electrodes 421a-d of extendable ECG electrode leads 460a-d are positioned on patient "p", extended (if necessary) and attached to receptacles 450a-d on electrode lead set hub 410c.

Figure 5A:
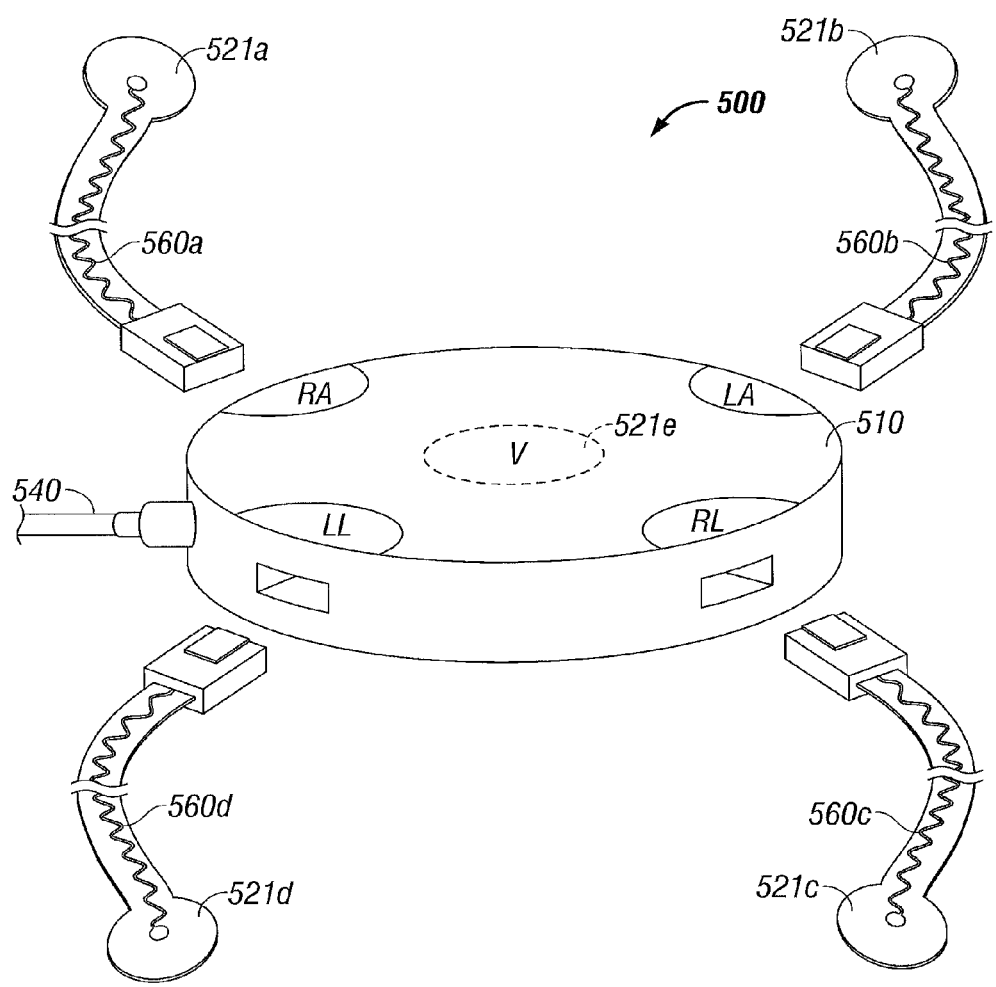
FIG. 5A is a schematic illustration of another embodiment of an ECG lead set assembly including stretchable ECG electrode leads.

FIG. 5A illustrates an ECG lead set assembly 500 with stretchable ECG electrode leads 560a-d. ECG lead set 500 includes lead set hub 510, cable 540 and a one or more stretchable ECG electrode assemblies 560a-d. The 5 electrodes 521a-e of the ECG lead set 402 are configured in a 5 lead configuration. ECG lead set 500 may be configured in other suitable configurations.

Lead set hub 510 may be formed of soft pliable material. Lead set hub 510 may include an adhesive or hydrogel patch or backing configured to hold the lead set hub 510 against the patient. Cable 540 connects lead set hub 510 to an ECG monitor (not shown) or to an ECG monitor adapter (not shown) configured to make ECG lead set 500 compatible with an otherwise non-compatible ECG monitor.

Figure 5B:
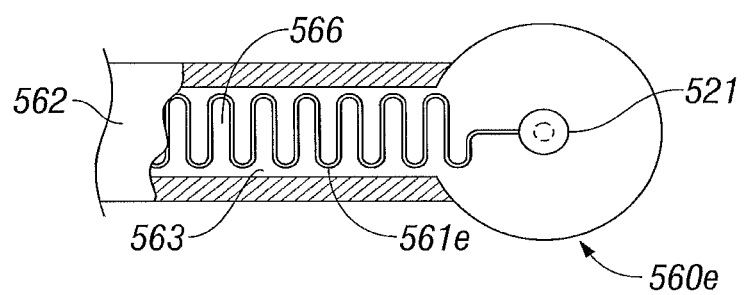
FIGS. 5B-5D are schematics illustrating alternate embodiments of stretchable ECG electrode leads useable with the ECG lead set assembly of FIG. 5A.

FIG. 5B illustrates a portion of a stretchable ECG electrode lead 560e with an undulating shaped wire 561e held between two stretchable attached insulating layers 562, 563, and forming a chamber 566. As the stretchable ECG electrode lead 560e is stretched, insulating layers 562, 563 stretch to the new length and at least a portion of the undulating shaped wire 561e within the chamber 566 between the insulating layers 562, 563 may straighten.

Figure 5C:
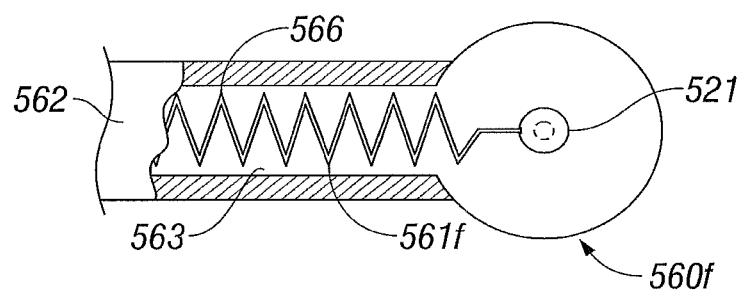

FIG. 5C illustrates a portion of stretchable ECG electrode lead 560f with a zigzag shaped wire 561f. As the stretchable ECG electrode leads 560f is stretched, at least a portion of the zigzag shaped wire 561f straightens.

Figure 5D:
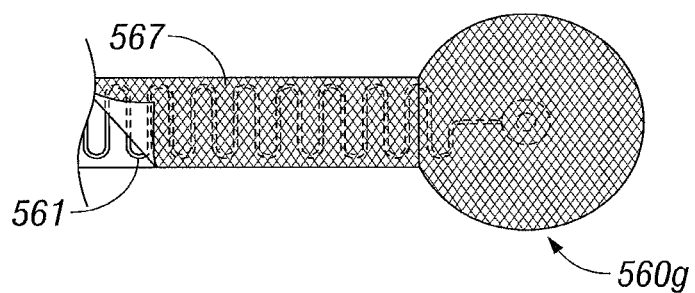

FIG. 5D illustrates the addition of shielding layer 567 to stretchable ECG electrode lead 560g of FIG. 5B. Shielding layer 567 may be formed from a stretchable mesh material with sufficient EMI shielding properties. Alternatively, undulating shaped wire 561 may include a shield.

Figure 6:
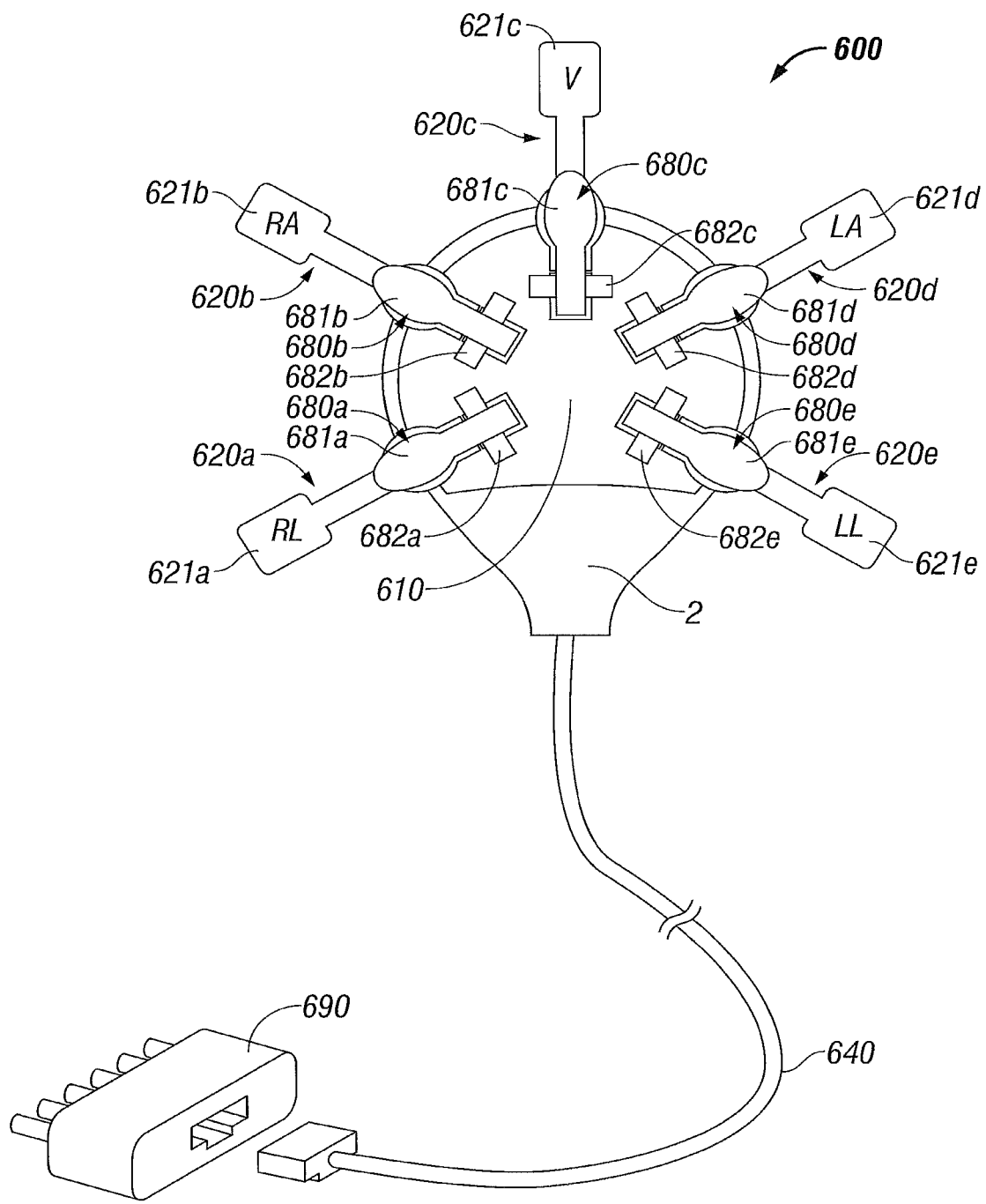
FIG. 6 is a schematic illustrating an ECG lead set assembly including a lead set hub with clamp receptacles.

FIG. 6 illustrates yet another embodiment of an ECG lead set assembly 600 of the present disclosure. ECG lead set assembly 600 includes lead set hub 610, at least one ECG electrode lead and a cable configured to connect the ECG lead set assembly 600 to an ECG monitor (not shown) or to ECG monitor adapter 690. ECG lead set assembly 600 is configured have the 5 electrodes 621a-e positioned in a 5 lead configuration. ECG lead set assembly 600 may be configured for other suitable configurations.

Lead set hub 610 includes at least one clamp receptacle 680a-e configured to receive an ECG electrode lead 620a-d. Clamp receptacle 680a-e includes a receptacle lever 681a-e hingedly attached to lead set hub 610 by receptacle pin 682a-e. ECG electrode lead 620a-e is fixedly disposed in clamp receptacle 680a-e when the receptacle lever 680a-e is in a clamped or actuated position, as illustrated in FIG. 6.

Figure 7A:
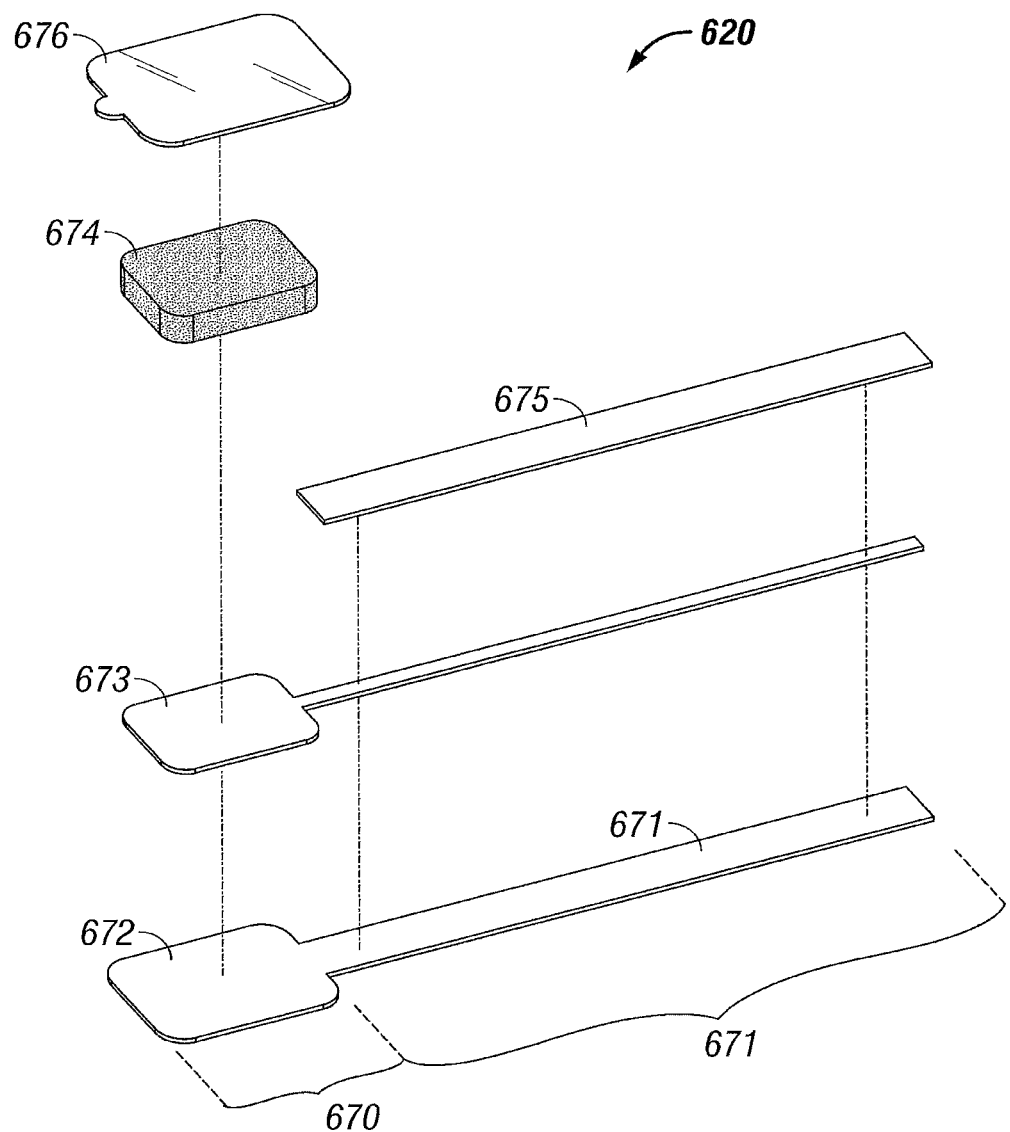
FIG. 7A is a an exploded view of the ECG electrode assembly of FIG. 6.

FIG. 7A is an exploded view of ECG electrode lead 620 of FIG. 6. ECG electrode lead 620 includes electrode tab 670 and flexible tail 671 which is about 12" to 18" in length. ECG electrode lead 620 is formed from substrate 672 at least partially covered with conductive ink coating 673, conductive adhesive hydrogel layer 674, insulating layer 675 and releasable liner 676. Conductive ink coating 673 is applied to, or printed on, substrate 672. Conductive ink coating 673 covers a substantial portion of the electrode tab 670 and forms a continuous strip down the center of substrate 675 from the electrode tab 670 to the proximal end of tail 671. Conductive adhesive hydrogel layer 674 is disposed on conductive ink coating 673 on electrode tab 670 and insulating layer 675 is disposed on conductive ink coating 673 on tail 671. Adhesive hydrogel layer 674 may be covered with a releasable liner 676.

Insulating layer 674 may be partially coated with a second adhesive layer (not shown) to adhere the ECG electrode assembly 620 to patient and maintain a low profile and to minimize lead movement.

Figure 7B:
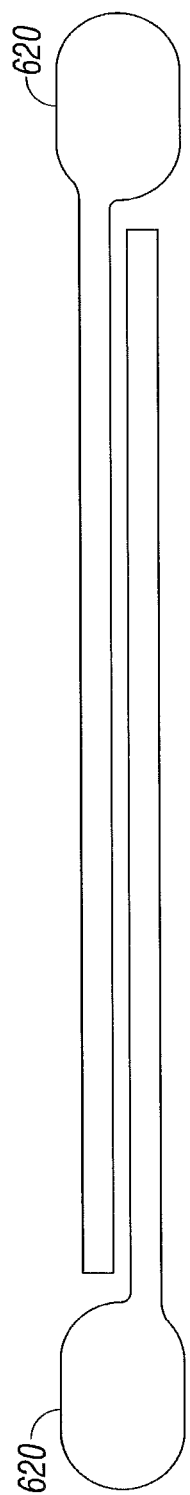
FIG. 7B is a schematic illustrating a method of manufacturing the ECG electrode assemblies of FIG. 7A.

ECG electrodes lead 620 may be manufactured as illustrated in FIG. 7B. Manufacturing ECG electrode lead 620 with tip 670 to tail 671 eliminates waste material. ECG electrode leads 620 may be die-cut into individual units or a perforated cut between ECG electrode leads 620 may allow clinician to remove ECG electrode leads 620 as needed.

Figure 8:
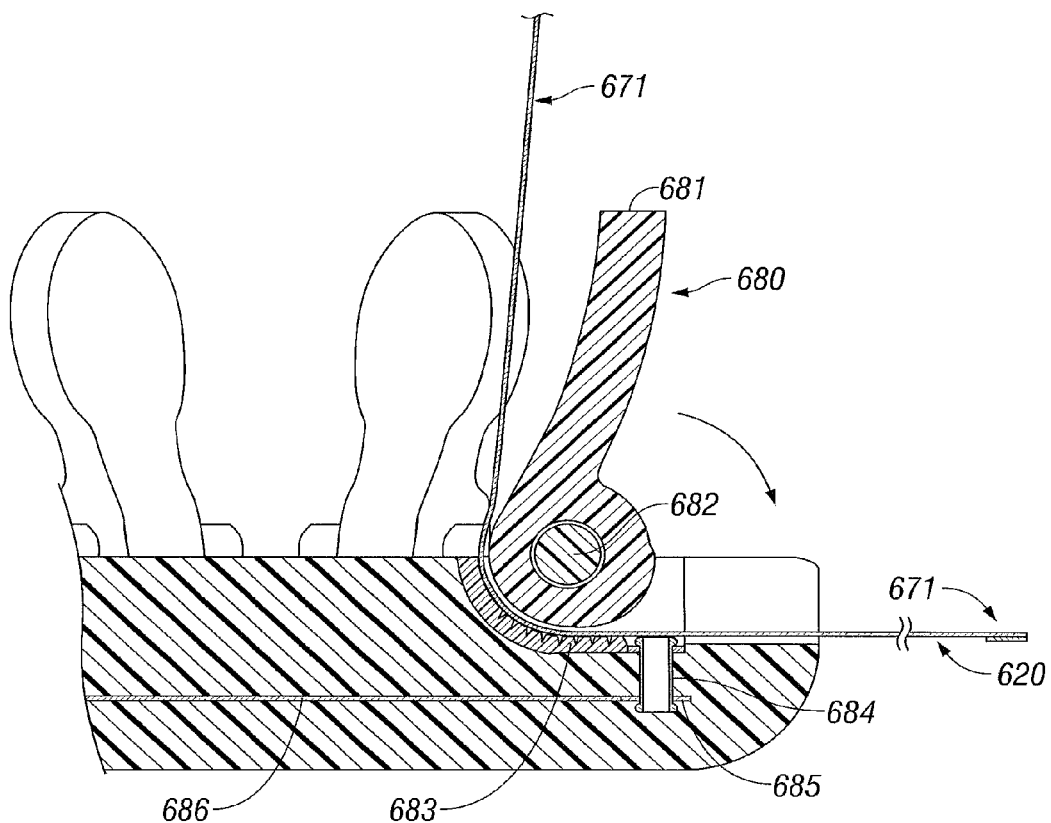
FIG. 8 is a cross-sectional view of the clamp receptacle of the lead set hub of FIG. 6.
Figure 9:
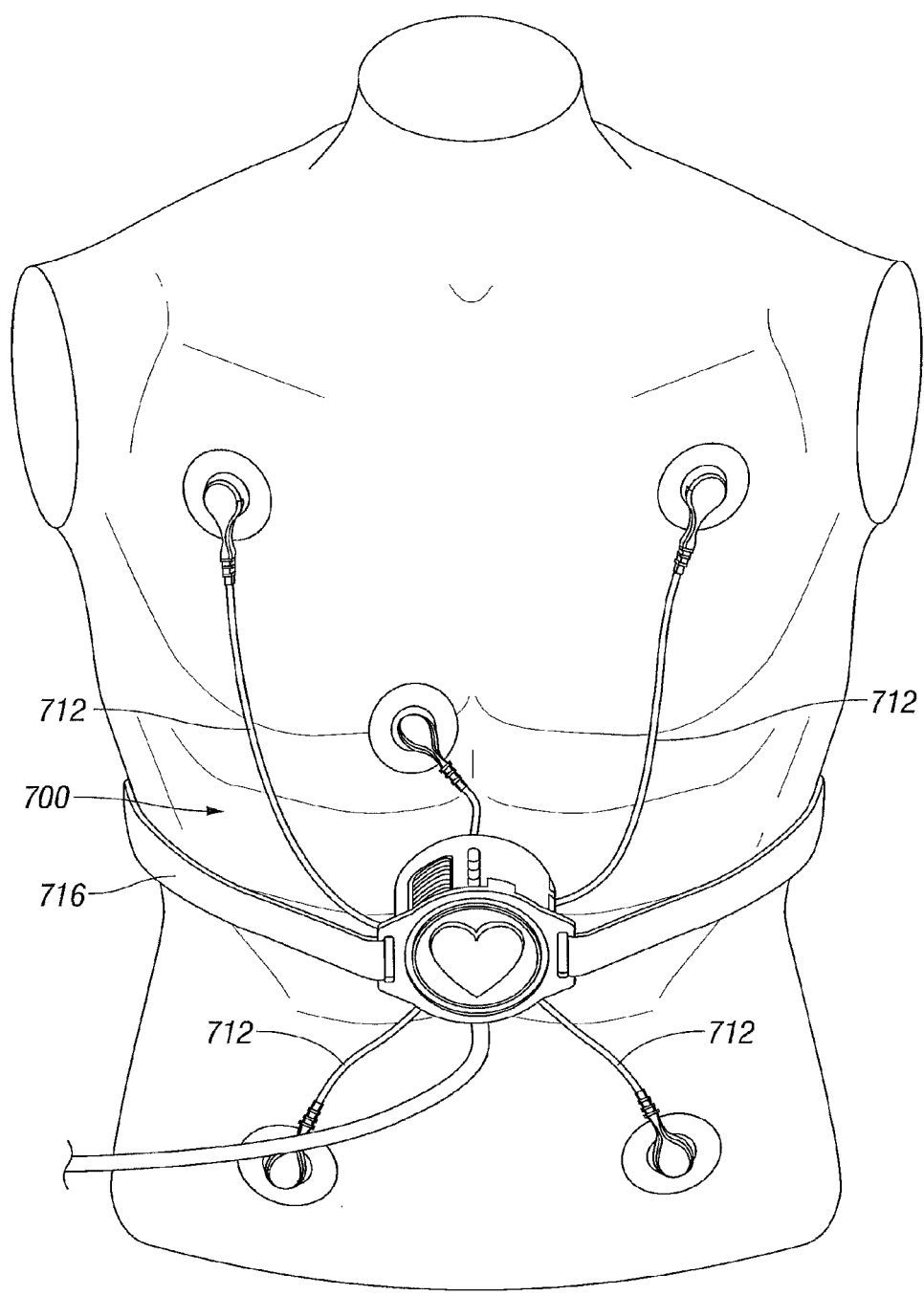
FIG. 9 is a schematic view illustrating another alternate embodiment of an ECG lead set assembly disposed on a patient.

In FIG. 8 receptacle lever 680a-e is in an up position and ECG electrode lead 620a-e is slidably disposed in clamp receptacle 680. ECG electrode lead 620 is disposed between diamond plate 683 and lower portion of receptacle lever 681. Diamond plate 683 is electrically connected to receptacle conductor 686 through ring termination 685 and rivet 684. Actuation or movement of the receptacle lever 681 about pivot pin 682 from an up position to a down position, as indicated by the curved arrow, presses a portion of the ECG electrode lead 680 against the diamond plate 683.

With reference to FIGS. 6 and 8, to lock ECG electrode assembly 620 in place, receptacle lever 681 is engaged to press at least a portion of tail 671 against the diamond plate 683, abrading or puncturing the insulating layer 675 and exposing at least a portion of the conductive ink coating 673 on tail 671. The exposed portion of conductive ink coating 671 makes electrical contact with diamond plate 683 thereby forming a connection between ECG electrode assembly 620 and receptacle conductor 686 through the diamond plate 683, rivet 684 and ring termination 685. When receptacle lever 681 is fully rotated, the excess tail 671 material is cut and may be removed.

In yet another embodiment of the present disclosure, connection point is a plastic buckle that has an elliptical hole in its mid section. Affixed to the base of the hub under the buckle is an elliptical post. A multi-conductor flex circuit has its conductors branch out to each connection point. At the end of each flex circuit branch is an elliptical hole with conductive ink around its circumference that is positioned at the base of the elliptical post. The tail end of the lead also has an elliptical hole with conductive ink around its circumference that loads onto the post, lying on top of the flex circuit branch. After the lead is loaded onto the post, the buckle is snapped down, sandwiching the end of the lead tail against the flex circuit conductor.

In a further embodiment of the present disclosure, cable 640 of the ECG adapter system 300 may include a plurality of layers to electrically shield the wires of the web 360 from electrical interference or noise. Alternatively, lead wires 320a-320e that form the web 360 may be individually shielded.

Figure 10A:
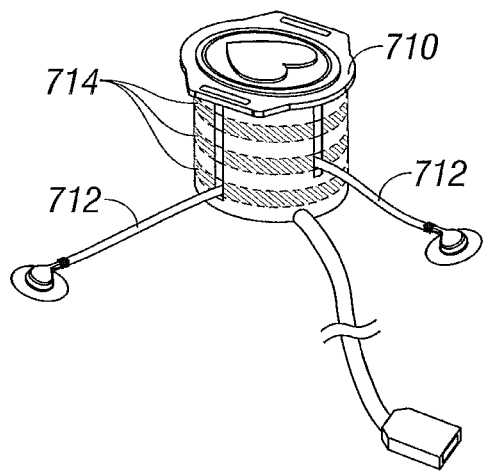
FIGS. 10A-10D are schematics illustrating the lead set hub and the ECG electrode leads of FIG. 9.
Figure 10B:
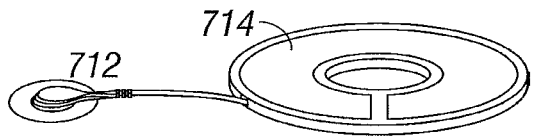
Figure 10C:
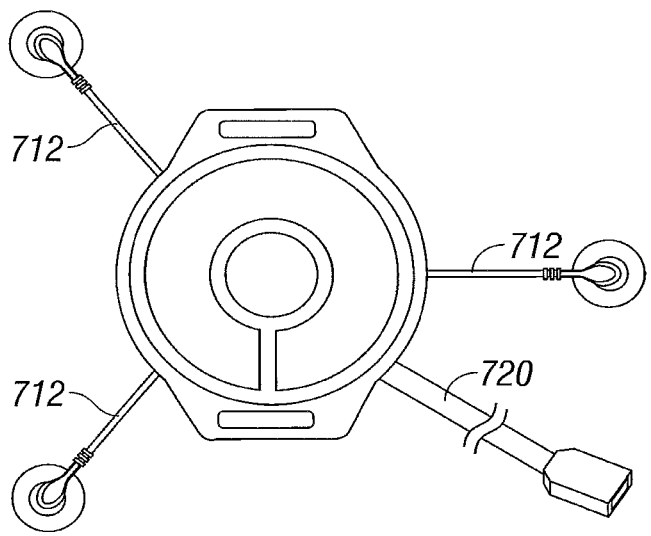
Figure 10D:
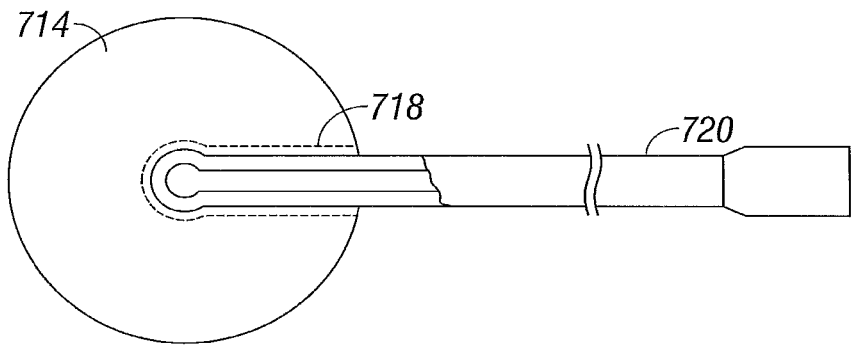

FIGS. 9 and 10A-10D illustrate an alternate embodiment of an electrode lead set assembly 700 of the present disclosure. Lead set assembly 700 includes lead set hub 710 and a plurality of electrode leads 712 extending from the lead set hub 710. Lead set hub 710 includes a plurality of retractable reels 714 which permit selective extension and retraction of individual electrode leads via an access hole in the hub. Alternatively, a hand crank can be positioned with respect to the lead set hub 710 to simultaneously wind the reels 714. Lead set hub 710 optionally has belt 716 attached thereto which is adapted for coupling to the patient "p" (e.g., about the torso or limb) to secure lead set assembly 700 relative to the patient "p". Belt 716 may be elastic or have a buckle (not shown) for length adjustment. Alternative means of fixation of the hub to the patient include an adhesive patch on the bottom of the hub or an adhesive hydrogel that permits repositioning without loosing significant tack. FIGS. 10A-10C illustrate one embodiment of lead set hub 710. In this embodiment, three reels 714 with electrode leads 712 are incorporated within the lead set hub 710 and arranged in stacked relation as shown. Reels 714 each may incorporate a light spring mechanism to provide for automatic retraction of electrode leads 712 and may further incorporate a releasable stop mechanism to releasably secure an electrode lead 712 at a predetermined length. Such reel mechanisms have automatic retraction and/or releasable securement capabilities are appreciated by one skilled in the art. As illustrated in FIG. 10D, the lower surface of lead set hub may have recess 718 to accommodate cable 720 which leads to the monitor. This presents a flat surface upon which lead set hub 710 may be positioned relative to the patient. Reels 714 may revolve about a central column. Alternatively, lead set hub 710 may be devoid of a central post or column. With this arrangement, stacked reels 714 may be retained within lead set hub 710 and spin within the lead set hub 710 as constrained by the internal surface of the hub 710, i.e., not about a central post or column. With this arrangement, lead set hub 710 includes a central opening where the column or post would reside. The opening is in axial alignment with the central openings of stacked reels 714. Recess or channel 718 receives the lead wires of cable 720 which extend up through the central opening for connection to their respective reels. The respective lead wires extend as a group from recessed channel 718 to a jacket or overmolded piece and eventually to a monitor connector. Through removal of a central post, the dimensioning of lead set hub 702 may be minimized.

Figure 11:
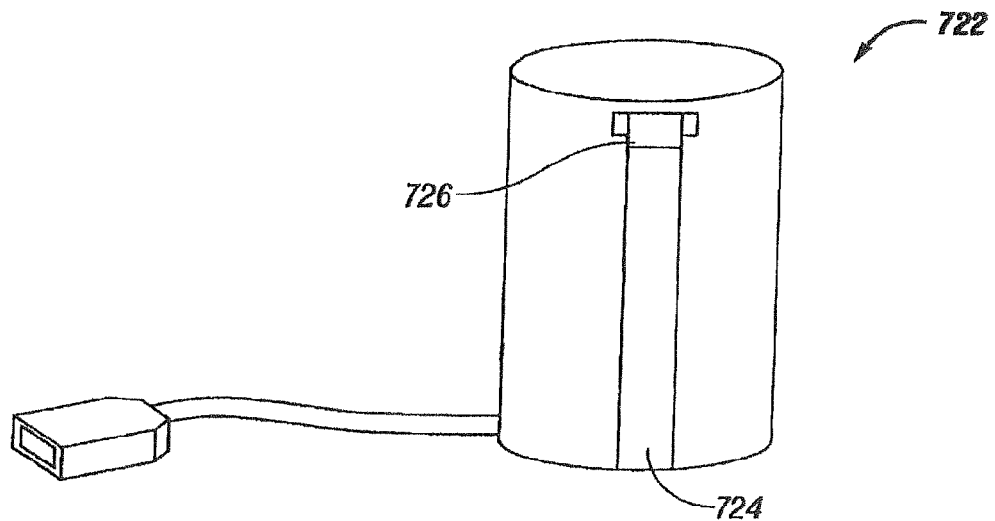
FIG. 11 is a side view of an embodiment of a central post for use with the lead set hub of the lead set assembly of FIG. 9.
Figure 12:
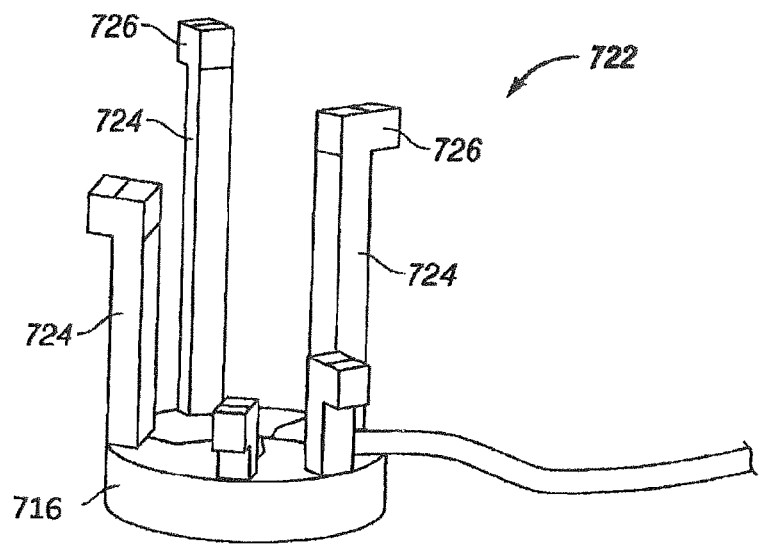
FIG. 12 is a side view with portions cut away of the central post of FIG. 11.

FIGS. 11-12 illustrate an alternate embodiment where lead set hub 702 is provided with central post 722 around which stacked reels 714 (see, e.g., FIG. 10A) spin. Central post 722 includes individual conductive elements 724 extending from base 716 of the central post 722. Conductive elements 724 are arranged at different heights in alignment with a specific reel 714 to contact the respective reel 714, i.e., each conductive element 724 is assigned to a specific reel 714 and is positioned to electrically contact with a corresponding inner contact surface of the respective reel 714. Preferably, each conductive element 724 incorporates projecting contact element 726 which contacts a contact surface of a reel 714. The remaining portion of conductive element 724 is recessed to avoid contact with the remaining reels 714 in lead set hub 702.

Figure 13:
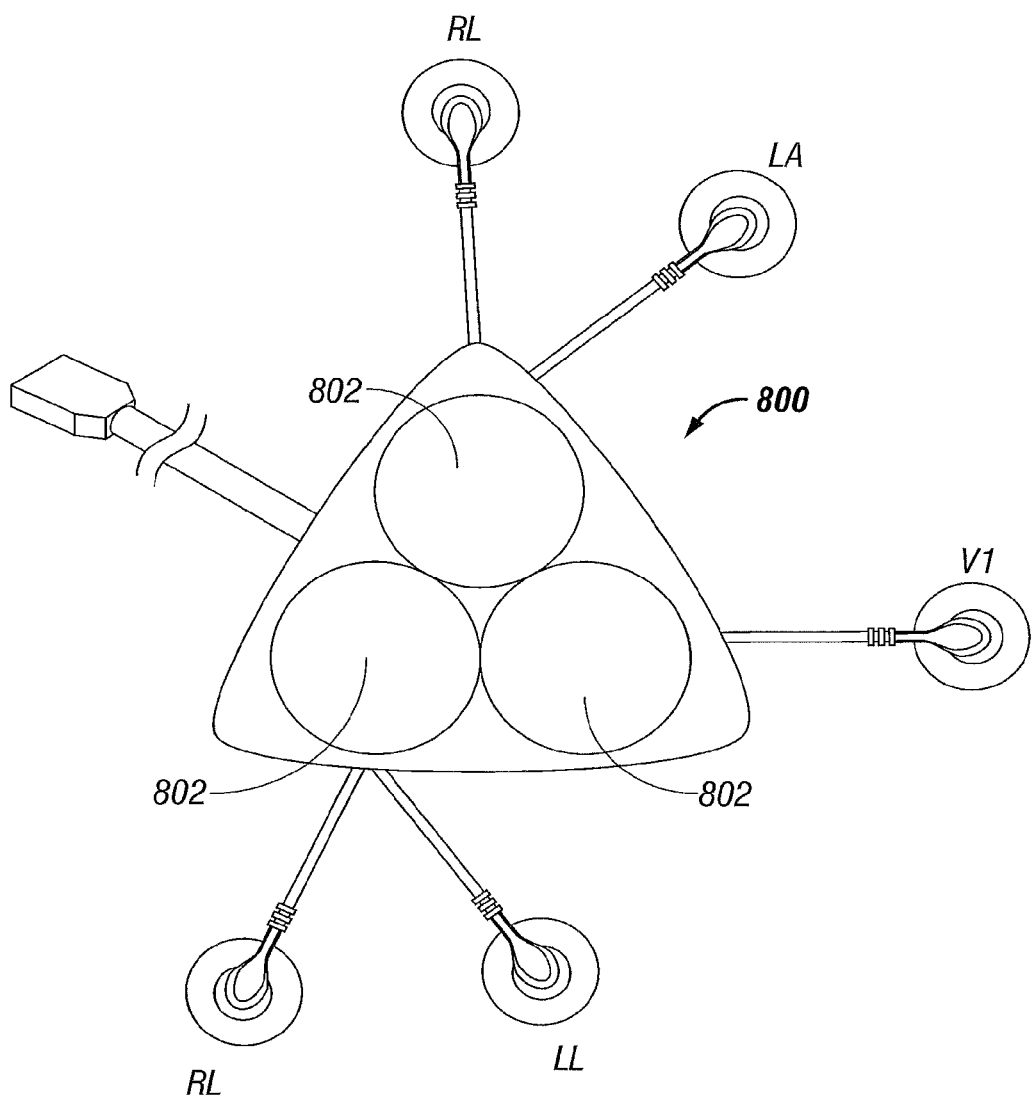
FIG. 13 is a schematic illustrating an alternate embodiment of a lead set hub for use with the electrode lead set assembly of FIG. 9.

FIG. 13 illustrates an alternate embodiment where the reels 800 are positioned within lead set hub 810 in side by side relation.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrode lead set assembly comprising:
a lead set hub comprising:
   a post comprising
      a base disposed at one end of the post; and
      a plurality of individual conductive elements directly connected to and extending from the base, the conductive elements disposed around the periphery of the base, each conductive element comprising a respective one contact element of a plurality of contact elements; and
a retractable reel assembly retained within the lead set hub, the retractable reel assembly comprising:
   at least three reel members adapted for rotation within the lead set hub; and
   an electrode lead wrapped about each reel member and having an electrical conductor for connecting to an electrode for receiving biopotential signals from a patient, each electrode lead being extendable from the corresponding reel member upon rotation thereof within the lead set hub, each reel member of the reel assembly being mounted about the post in rotational relation therewith and each reel member being in electrical contact with a corresponding one contact element of the plurality of contact elements.

2. The electrode lead set assembly according to claim 1, further comprising a spring mechanism associated with at least one reel member, the spring mechanism configured to retract the electrical lead about the lead set hub.

3. The electrode lead set assembly according to claim 2, further comprising a releasable stop mechanism associated with at least one reel member, the releasable stop mechanism configured to releasably secure the electrode lead at a predetermined length extended from the at least one reel member.

4. The electrode lead set assembly according to claim 1, wherein the lead set hub defines at least one channel in an outer wall thereof, the channel permitting passage of the electrode lead of at least one reel assembly.

5. The electrode lead set assembly according to claim 4, wherein the lead set hub includes a plurality of channels in the outer wall for permitting passage of the electrode leads of respective reel assemblies.

6. The electrode lead set assembly according to claim 5, wherein the channels are arranged in radial spaced relation.

7. The electrode lead set assembly according to claim 1, wherein the conductive elements are arranged to depend from the base at varying distances to be aligned with corresponding reel assemblies in the lead set hub to electrically connect with the electrode leads of the corresponding reel assemblies.

8. The electrode lead assembly according to claim 7, wherein each conductive element comprises a recessed portion directly connected to the base and a projecting portion projecting away from the recessed portion to enable the contact element to contact a contact surface of a corresponding reel assembly.

9. The electrode lead set assembly according to claim 1, further comprising a belt attached to the lead set hub, the belt being adapted for coupling the lead set hub to the patient.

10. The electrode lead set assembly according to claim 1, wherein the lead set hub includes an adhesive patch for attaching the lead set hub to the patient.

* * * * *